US006645210B2

(12) United States Patent
Manderson

(10) Patent No.: US 6,645,210 B2
(45) Date of Patent: Nov. 11, 2003

(54) ROD IMPLANT FOR OSTEOSYNTHESIS OF LONG BONES

(76) Inventor: Easton L. Manderson, 1750 Sir Galahad Way, Ashton, MD (US) 20861

( * ) Notice: Subject to any disclaimer, the term of this patent is extended or adjusted under 35 U.S.C. 154(b) by 0 days.

(21) Appl. No.: 10/198,610

(22) Filed: Jul. 19, 2002

(65) Prior Publication Data

US 2002/0183753 A1 Dec. 5, 2002

Related U.S. Application Data

(62) Division of application No. 08/494,678, filed on Jun. 26, 1995, now abandoned.

(51) Int. Cl.⁷ .......................... A61B 17/70; A61B 17/80
(52) U.S. Cl. ............................................ 606/69; 606/60
(58) Field of Search ............................ 606/60, 62, 63, 606/64, 67, 69

(56) References Cited

U.S. PATENT DOCUMENTS

| | | | | |
|---|---|---|---|---|
| 3,695,259 A | * | 10/1972 | Yost | 606/69 |
| 4,573,458 A | * | 3/1986 | Lower | 606/69 |
| 4,923,471 A | * | 5/1990 | Morgan | 606/60 |
| 5,147,361 A | * | 9/1992 | Ojima et al. | 606/61 |
| 5,336,224 A | * | 8/1994 | Selman | 606/69 |
| 5,415,661 A | * | 5/1995 | Holmes | 606/69 |
| 5,474,553 A | * | 12/1995 | Baumgart | 606/71 |
| 5,527,310 A | * | 6/1996 | Cole et al. | 606/60 |
| 5,569,246 A | * | 10/1996 | Ojima et al. | 606/61 |
| 5,947,965 A | * | 9/1999 | Bryan | 606/61 |

* cited by examiner

Primary Examiner—David J. Isabella
(74) Attorney, Agent, or Firm—Antonelli, Terry, Stout & Kraus, LLP

(57) ABSTRACT

Described is a solid rod implant having a pair of plates at each end of the rod which is designed for bridging two portions of a broken long bone, united or ununited, and maintaining the divided portions of the bone in rigid alignment with each other. The solid rod implant may be rigidly attached to the damaged long bone by means of the pair of partly tubular plates at either end of the rod. These plates provide the sole means of attachment of the implant to the bone i.e there is has no provision for any attachments along, beside or through any portion of the rod that would allow it to be apposed to, or attached to any portion of the bone to which it is providing support during osteosynthesis. By its design and method of rigid attachment to the bone, through partly tubular end plates, the implant allows controlled motion at the fractured or non united portions of the bone fragments, a motion which stimulates rapidly forming external bridging callus formation for osteosynthesis of the long bone, a process that shortens the time of osteosynthesis of long bones so treated.

16 Claims, 5 Drawing Sheets

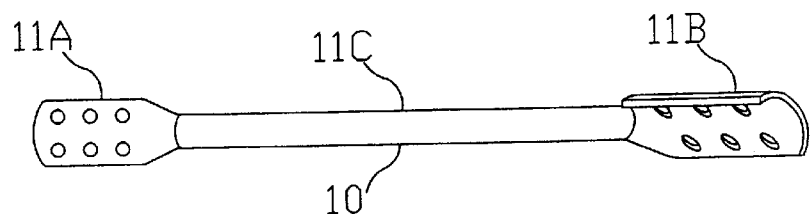
FIG. 1A
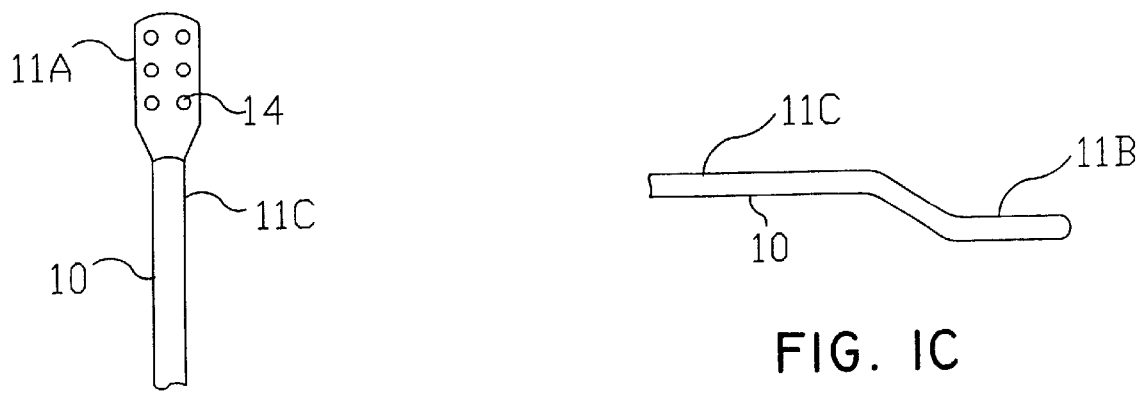
FIG. 1B
FIG. 1C
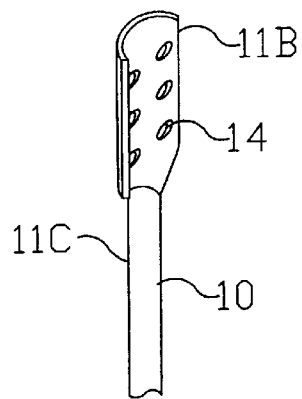
FIG. 1D

ROD IMPLANT FOR OSTEOSYNTHESIS OF LONG BONES

CROSS REFERENCE TO RELATED APPLICATIONS

This is a divisional application of application Ser. No. 08/494,678 filed Jun. 26, 1995, now abandoned, for "Instrument for osteosynthesis of Long Bone Fractures—Manderson Side Binder Implant," co-pending application Ser. No. 09/343,180 filed Jun. 30, 1999, for Extramedullary Implant for Long Bones and co-pending application Ser. No. 09/764,058 Extramedullary Rod Implant for Long Bones filed Jan 16, 2001.

The present invention generally relates to an implant to be used for internal fixation of bone fragments to effect osteosynthesis of ununited bone fragments. The implant is particularly suitable for fractures of long bones although it may be adaptable to bridge joints of long bones requiring arthrodesis or bones in a state of non union, malunion or pseudoarthrosis.

BACKGROUND OF THE INVENTION

It is well known in the art of bone fixation that the repair of fractured bones may be accomplished by the attachment of bone plates and intramedullary nails or rods to the injured bone to hold the fractured bone ends in place during healing. Bone plates and intramedullary rods or nails are designed to provide rigid fixation and support for applied loads while being subjected to cyclical loads in tension, compression, torsion and or bending.

Bone plates are generally described as devices with at least one flattened surface and with holes or grooves for screws and wires, respectively, situated in or along the main body of the plate, to allow fixation of the flattened surface of the device to the bone surface by means of screws or wires for the purpose of holding the bone in place and achieve union of the bone fragments.

The bone plates traditionally are rigidly fixed to the bone to prevent motion between the fragments. Empirically bone union occurs with rigid fixation, but rigid fixation of the bone fragments along significant lengths and breaths of the bone will weaken the bone through stress shielding and disuse atrophy. The adverse effects of stress sheilding and disuse atrophy are prolonged healing time and refracture or discontinuity of the bone if the device is removed after osteosynthesis.

Other adverse effects of plates are as follows: Healing also is generally without the formation and protective function of external callus; applying the plate for rigid fixation requires surgical dissection of the non-osseous tissues, a process which injures the external vascular and nutritional sources of the bone fragments and which may be imprudent in the presence of preceding traumatic injury to the bone and non osseous tissue.

Screw holes of plates are weak points or stress risers that may cause failure or breakage of the plate during load application especially if this load application is repetitive or cyclical. If a plate does not have fixation applied throughout its entire length, fixation may be inadequate for load support during load application which is usually in several planes, a situation that may result in loss of axial and rotational alignment, malunion or nonunion of the fragments and or failure of the device along the stress rising non utilized screw holes. Needless to say, if several screw holes are left unused then the remaining portion of the plate is usually not rigid enough to withstand cyclical applied loads without failure or deformation.

Generally, the loading configuration to which an implant is subjected is not limited to one particular plane. There may be simultaneous forces in several planes. If this is the case, cross sections which are asymmetrical may not be as satisfactory as those which are symmetrical for load bearing purposes. Thus, a plate which is usually flattened on one or more surfaces will not bear loads equally in all directions and may be adequate to withstand forces in one direction but inadequate to withstand forces in another. By comparison a round section device has equal properties for load distribution and bearing in all directions.

Intramedullary nails or rods are commonly used to support long bone fragments to effect osteosynthesis. The rod has several advantages over the plate. Placement can be subcutaneous at an entry point to the intramedullary canal of the long bone thereby avoiding surgical injury to the extra osseous tissues that provide nutritional and vascular support to the bone fragments especially in times of injury thereby lessening the risk of infection. Unlike plates, they share functional loading in weight bearing during and after the osteosynthesis process thereby preventing disuse atrophy as seen with plate fixation for osteosynthesis. This feature makes a second operation for removal to allow functional load distribution to the bone often unnecessary. If removal is necessary, refracture of the bone is uncommon, unlike the case with removal of plates, because the functional capacity for load bearing returns to the bone during and after healing and before removal, since the rod shares function with the bone to which it is applied, thereby avoiding stress shielding of the bone.

For intramedullary osteosynthesis of long bones, the rod or nail may be rigid, flexible, circular, diamond shaped, rectangular, of open section or closed section. However, it has been proven that for a given cross sectional area, a closed circular configuration with symmetry in all directions is most reliable in sustaining forces applied in several planes.

The intramedullary rod or nail conventionally applied, has several disadvantages. Insertion technique has a steep learning curve and can be technically demanding and requires expensive and sophisticated equipment and well trained support personnel. Positioning of the patient must be precise to allow proper insertion and this is not always possible or practical for a seriously multiple injured or obese patient. The use of the intramedullary rod or nail is limited, almost precisely to treating the diaphyseal section of the long bone needing osteosynthesis.

Although axial alignment is usually assured with intramedullary rods or nails, rotational alignment is not assured unless the rod has a fluted end or unless the rod is locked proximally or distally with screws, a procedure that is difficult to do in the distal locking area. Because of the great difficulty in achieving precise screw placement, this step usually prolongs the operative time and time of exposure to radiation, consequently, intramedullary rodding or, nailing must be performed using fluoroscopy, to ensure precise placement.

SUMMARY OF THE INVENTION

In general, application of a strong, rigid rod for intramedullary placement for osteosynthesis of a long bone requires intramedullary reaming, a process that entirely destroys the inner ⅔ of the intramedullary vascular circulation to the diaphysis of the long bone. The outer ⅓ of the diaphysis is supplied by the external non osseous tissue. If this is also disrupted by injury at the time of reaming for nail or rod insertion then the undesirable situation of the diaphysis being completely without vascular supply exists making the bone fragments more susceptible to infection or the chances of union more unlikely.

If the rod is placed without reaming then the constraints of the intramedullary canal limits the diameter size of the rod or nail, a situation that may make it too thin and flexible for effective load bearing or support such as seen in cyclical weight bearing.

Moreover, after reduction of the fragments, the osteosynthetic device must be rigid enough to hold the fragments in the restored position and alignment during load application especially for the long bones of the lower extremity engaged in the cyclical load bearing of walking and for the long bones of the upper extremity engaged in cyclical load support as seen in crutch walking, for example.

The designer should make the device sufficiently rigid so as to provide no more than the maximal tolerable amount of relative motion during the healing process. Controlled motion at the non-united ends of the long bones is desirable to stimulate callus formation. The implant should also be rigid enough to withstand load sharing forces in all planes (compression, bending, twisting and tension), but not so rigid as to force the implant to continuously carry the load after healing has taken place since this situation would lead to fatigue failure of the implant. On the other hand, too much motion from a pliable or flexible rod could lead to a hypertrophic non-union in a long bone.

Considering the variation in anatomy and the biologic constraints on size of the device, the ideal osteosynthetic implant is difficult to select by material selection criteria only. However, in selecting an ideal device attention must be paid to factors including the combination of design, application, material selection, selection of cross sectional areas and lengths in broad categories such as small, medium and large. The device should meet ideals of minimal soft tissue damage during application, rapid application with very limited amount and use of sophisticated equipment and personnel, load sharing with the bone fragments to which the device is applied, before and after osteosynthesis. In addition, the device will provide support for the rapid development of external callus driven by the stimulus of load sharing that causes controlled, benign motion at the ununited bone ends; rigidity and rigid fixation away from the bone ends that will allow controlled motion at the ununited bone ends while at the same time allowing load bearing and support, even of a cyclical nature. Further, the invention describes an implant for osteosynthesis that will initially bear the total load of the injured biologic structure, since the initial and basic purpose of this device, should be to provide a means of load transmission across fractures or ununited bone fragments before synthesis has been achieved.

In accordance with applicant's invention, it is possible to overcome the many defects attributable to intramedullary rodding and extramedullary bone plate fixation through the use of an extramedullary rod capable of being rigidly attached to the extremities of a long bone, provide weight bearing support to the bone along its longtudinal axis and permit stimulatory forces of motion that generate callus repair at the point of nonunion of the bone. An extramedullary rod of this type is unknown to those skilled in the art.

OBJECTIVES OF THE INVENTION

A principal object of this invention is to provide rigid fixation of the bone fragments that will maintain axial and rotational alignment during load bearing of osteosynthesis.

Another object of this invention is to provide a bone fixateur that is preshaped to accommodate the general anatomy of the bone fragments to which it is applied and restore normal or near normal axial and rotational alignment of the bone after union.

Yet another object of the invention is to allow functional load sharing throughout the fixation before osteosynthesis and after osteosynthesis.

A further object of the invention is for the device to be applied in a rigid manner to the bone fragments with minimal surgical damage to the soft tissues that are external and internal to the bone.

One more object of the invention is for it to be applied with little or no contact of the rod section to the bone fragments while still providing rigid support to the fragments for load bearing.

A final object of the invention is by design and application to provide a method that would allow beneficial motion at the ununited bone ends of long bones that will stimulate the formation of external bridging callus between the ununited bone ends.

BRIEF DESCRIPTION OF THE DRAWINGS

FIG. 1(A) is an enlarged [perspective] view of the implant instrument of the present invention showing the rod section, partially tubular end plates and screw holes.

FIG. 1(B) is an enlarged lateral view of a partially—tubular end—plate and rod and the confluent junction of the plate and rod.

FIG. 1(C) is an enlarged lateral view of the end plate of the device showing the relationship between the end plate and the rod section.

FIG. 1(D) is an enlarged end view of the of the instrument showing the substantially flat outer surface and the concave inner surface of the instrument.

DETAILED DESCRIPTION OF THE INVENTION

Figure 2A:
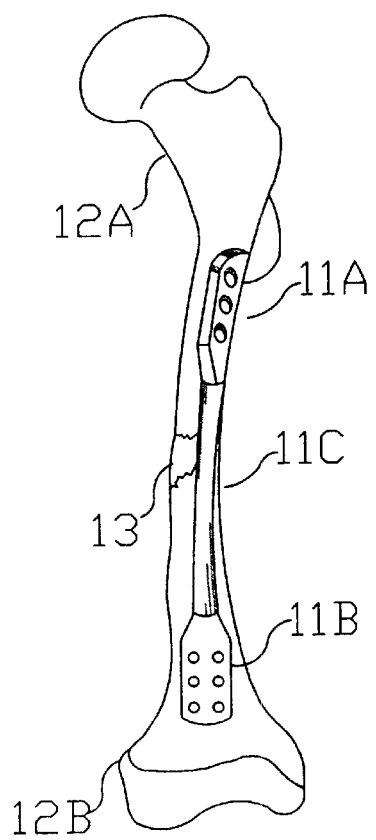
FIGS. 2(A) and 2(B) show the invention as applied to an instrument adapted for use on the femur showing a rod section connected to partially tubular end sections, with screw holes. The instrument is rigidity attached to the indamaged bone ends at a distance from th point of fracture.
Figure 2B:
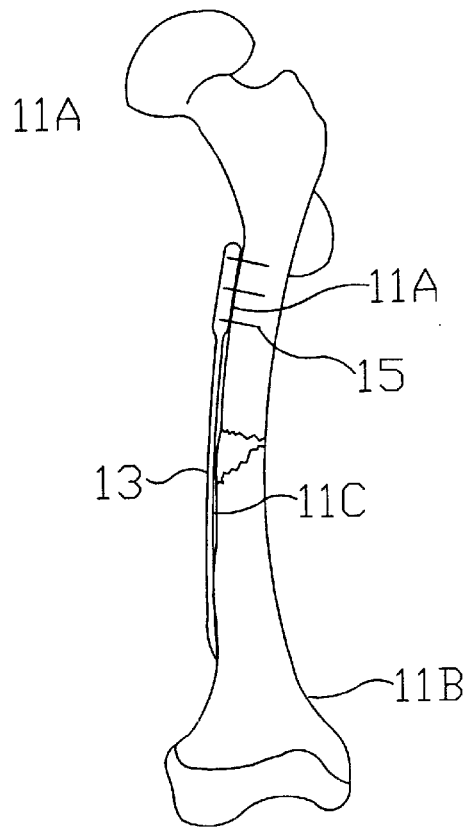
Figure 2C:
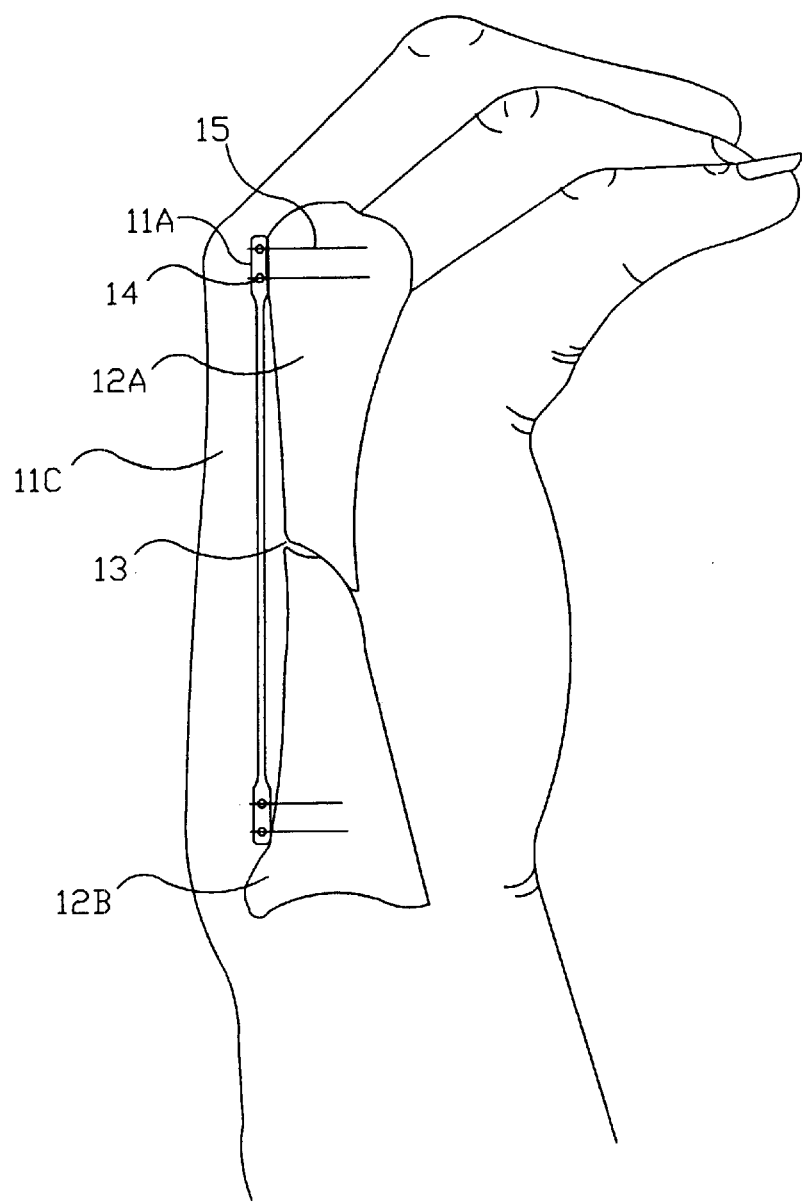
FIG. 2(C) shows the implant instrument in position for the repair of a phalangeal bone.
Figure 2D:
FIG. 2(D) is an enlarged end view of the partially tubular plate showing the concave orientation of the instrument and the pedicles for attachment of the end plate to the bone.
Figure 3A:
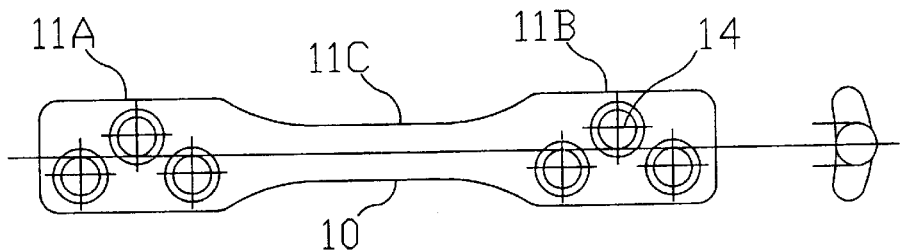
FIGS. 3A, 3B and 3C show forms of the device used in the repair of fractures of the ulnar, radial and wrist, respectively.
Figure 3B:
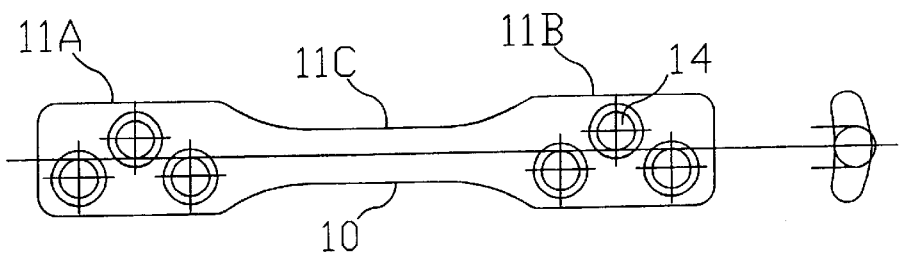
Figure 3C:
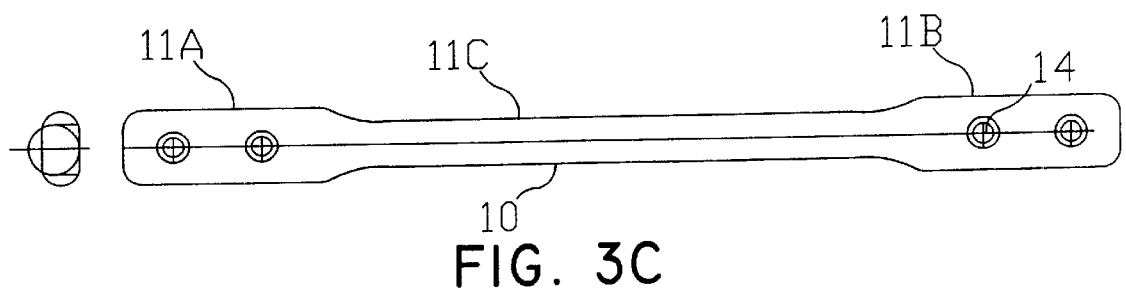
Figure 4A:
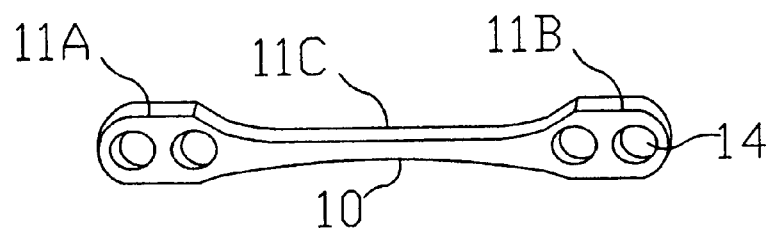
FIGS. 4A, 4B, and 4C are different sizes of the device for use on the phalangeal bones.
Figure 4B:
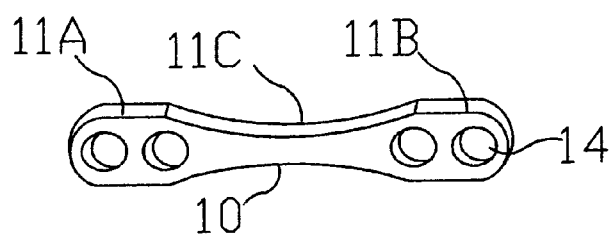
Figure 4C:
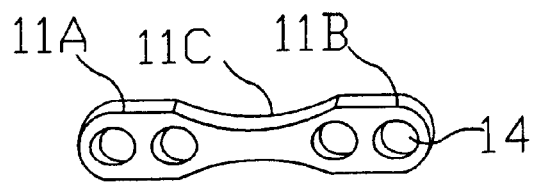

Referring to FIG. 1A there is shown a device having the numeral 10 made of a rigid inert material, such as stainless steel. The device 10 includes two identical substantially flat partially tubular plates end 11A and 11B with screw holes 14; and a middle rod section 11C which joins the end plates, 11A and 11B. FIG. 2A shows the device in place on a fractured femur 12, it will be noted that the middle rod section, 11C of the [device]—implant—spans the ununited bone fragments 13, of the femur 12 and the partially tubular ends of the device are attached to the distal and proximal sections of the injured bone 12A and 12B by means of screws 15.

Referring specifically to FIG. 2A it can be seen that in practice the implant 10 is held in place on the fractured bone, only at the extremities of the bone and that the implant is completely unattached to the fractured bone except by means of tubular end plates which are attached to the proximal and distal ends of the injured bone. Generally, however, each tubular end plate is designed to accommodate [two] up to five screw holes 14. The rod 11, portion of the implant spans the fractured area so that no screws or fixation devices are close to the fracture zone. This spanning feature, in turn, allows rigid fixation of the instrument at the ends while leaving the central portion of the bone unaffected by the preserve of the instrument. This unique method of fixedly attaching the instrument to the extremities of the bone, only generates micromotion at the ununited bone ends that encourages and sustains the more rapid healing due to external bridging callus formation, rather than the healing by the slower primary bone healing seen with rigid fixation. Since no dissection is done in the fractured area, and since the device is fitted extramedullary, there is no disturbance of the endosteal blood supply (inner ⅔ of the cortex) or the periosteal blood supply (outer ⅓ of the cortex).

As shown below, the device of this invention, 10 is designed in form and manner to fit on any of the long bones of the body, including the thigh, leg, arm, forearm and wrist bones. Each device will have a minor adjustment in form, shape or length to make it adaptable for the particular bone.

The femoral "sidebinder," for fractures of the femur (thigh) will vary on either the left or the right and may vary in lengths from approximately 10 inches to 12 inches.

Tibial "sidebinder" with respect to the treatment of fractures of the tibia, the (leg) is approximately 10 inches to 11 inches and is also adaptable left or right handed applications.

The Humeral "sidebinder," for fractures of the humerus comes in two lengths, one approximately 9 inches and 10 inches, and is adaptable to left and right.

(Forearm) the Radial "sidebinder," for fractures of the radius and (forearm) ulnar "sidebinder," for fractures of the ulnar are one size, only and the length is determined accordingly.

Wrist spanner (for fractures of the wrist), this instrument is one size only and has four holes, two in each tubular end plate.

The implant is designed to be implanted quickly and with minimum disturbance of the surrounding bone and tissue to facilitate early bone healing. Moving the plate sections away from the fracture line, as this implant does, decreases the rigidity of the plate fixation and allows for the maintenance of a stable but flexible environment in the region of the fracture. The flexibility also allows bending stress to be transmitted to the bone thereby preventing stress shielding. Further, because there are no stress rising holes in the spanning rod section, these implants can withstand cyclic loading such as crutchwalking for the humerus and weight bearing for the femur and tibia, without the need for additional external fixtures.

According to the procedure of this invention, the processes and techniques of intramedullary rod fixation are incorporated with those employed in extramedullary plate fixation to achieve results which have not been achieved previously.

In its preferred embodiment the implant is designed to treat femoral shaft fractures. The device is designed with anterior and lateral curves and its length will coincide with the length of the femur being repaired. The essential modifier in length selection is the length needed to span the fracture and injury site since surgical plate application should be well away from the fracture zone. The cylindrical section of the device may vary in diameter from 10 to 12 millimeters to correspond to the size and weight of the injured person.

The length of the nail selected for fixation of the device to the non-fracture bone ends may be modified according to patient size (length of femur), patient age (presence of growth plate), fracture grade (extent of comminution) and fracture pattern (transverse, oblique, spiral). Fixation may be accomplished by means of screws, nails or wire. If screws are used the type of screw may vary in length, diameter or screw type depending on the nature of the fracture, the advantages to be gained by using one type of screw over another and the overall needs of he patient. In general, the diameter of the screws may be selected from among the following: 2.7, 3.5, 4.5, 6.5, 7.0 millimeters.

Considering these factors the appropriate length of the implant can thus be selected by aligning the non-sterile implant on the injured extremity during restoration of femur length under fluoroscopy, on the non injured thigh before reduction or along radiographs of the injured or non injured femur.

In order to insert the instrument on a fractured bone, place patient supine on the fracture table using fluoroscopy to restore anatomic length to the injured femur, two lateral incisions, one distal and one proximal to the fracture zone are made in the outer skin in the injured femur. The incision is connected by means of a submuscular tunnel through which the implant is inserted with the curve anterior. Fix the plate sections to the lateral cortices temporarily by placing Steinmann pins through a plate hole in the distal and proximal end plates. To fix the plate permanently to the bone, it is recommended to place at least three screws place in each plate section.

For supracondylar fractures 6.5 cancellous screws can be used in the distal metaphyseal fragment. If the bone is osteoporotic the fixation can be augmented with bone cement. Proper rotation of the bone will usually be ensured with identical lateral placement of the plate sections. The wounds should be copiously irrigated with antibiotic solution and closed in layers in the usual fashion. Closed suction drainage is optional if proper hemostasis has been achieved. Apply sterile dressing and discontinue traction, if used preoperatively.

Postoperatively, the patient may sit up in chair or get out of bed as general condition allows. Continue appropriate broad spectrum antibiotics started

What I claim is:

1. A rod implant for osteosynthesis of fractured long bones, by placing and holding the ununited ends of said bones in fixed and constant alignment, and promoting the process of osteosynthesis and reunion of said fractured long bone, comprising:

solid cylindrical rod having a pair of substantially flat, partly tubular fixation plates at each end of said rod, said fixation plates having fastener receiving openings for fastening said implant to the extremities of said fractured long bone, said fixation plates having a concave inner surface for fastening said plate to the curved surface of said fractured bones, said cylindrical rod being contoured to the shape and length of the particular bone to which it is to be fastened, said fixation plates and said cylindrical rod lying in different planes with respect to each other so that upon fastening of said tubular plates to said fractured bone said cylindrical rod is placed in parallel, non-contact alignment with the fractured long bone to which it is fastened and provides weight bearing support for said fractured long bone along the longtudinal axis thereof, said implant being of such length as determined according to the pre-fracture length of said long bone to which it is to be attached so that upon fastening and alignment of said implant on said fractured bone said fractured bone is restored to its approximate pre-fracture length, said fastener receiving openings being generally adapted to receive a fastening members therein.

2. A rod implant as claimed in claim 1, wherein the length and contour of said implant is substantially the same as the length and contour of the fractured long bone to which it is to be fastened.

3. A rod implant as claimed in claim 1, wherein said cylindrical rod is offset from a plane intersecting said flat fixation plates.

4. A rod implant as claimed in claim 1, wherein:
the fixation plates are a pair of identical partly tubular plates;
the cylindrical rod is narrower than said tubular plates; and
a diameter of said cylindrical rod and the angular orientation between said cylindrical rod and said tubular plates corresponds to the particular long bone which is to be stabilized and a position of the bone fragment to which the fixation plates are to be attached.

5. A rod implant as claimed in claim 1, wherein:
if the long bone is a femur, the maximum length of said implant is 12 inches, and if the long bone is a wrist bone, the minimum length of said implant is 2 inches; and
if the long bone is a femur, each of said tubular plates has a maximum of five receiving openings, and if the long bone is a wrist bone, each of said tubular plates has at least one receiving opening.

6. A rod implant as claimed in claim 1, wherein said cylindrical rod of said implant has a uniform cross-sectional width throughout the length thereof and wherein said tubular plates at each end of said cylindrical rod have a wider cross-sectional width diameter than said cylindrical rod.

7. The rod implant as claimed in claim 1, wherein said implant has a contour corresponding to a curvature, alignment and length of the long bone to which it is to be attached.

8. The rod implant as claimed in claim 1, wherein said tubular plates and said cylindrical rod are constructed in one piece and said tubular plates are generally rectangular in shape.

9. The rod implant as claimed in claim 1, wherein:
said tubular plates at each end of said solid cylindrical rod and said solid cylindrical rod are in alignment with the end of the bone to which it is to be attached, and
an angle between said solid cylindrical rod and said tubular plate corresponds to an angle between said tubular section and the fractured bone fragment to which it is to be attached.

10. The rod implant as claimed in claim 1, wherein:
said implant is formed of a pliable material.

11. A rod implant according to claim 1, wherein said implant is made formed of an inert material.

12. An implant for setting a fractured bone, comprising:
a substantially rigid rod having a first end and a second end, opposed to the first end, and having a longitudinal axis extending between the first and the second ends; and only a single pair of attachment members configured to attach the implant to the fractured bone, wherein a first of the pair of attachment members is connected to and extends beyond the first end of the rod in a first direction substantially parallel to the longitudinal axis, and a second of the pair of attachment members is connected to and extends beyond the second end of the rod in a second direction substantially parallel to the longitudinal axis;

wherein the first attachment member has a first plate portion having a first angle of curvature about a first curvature axis substantially parallel to the longitudinal axis, and the second attachment member has a second plate portion having a second angle of curvature about a second curvature axis substantially parallel to the longitudinal axis.

13. The implant according to claim 12, wherein the rod and the single pair of attachment members are integrally formed of a homogeneous material.

14. An implant for setting a fractured bone, comprising:
a substantially rigid rod having a first end and a second end, opposed to the first end, and having a longitudinal axis extending between the first and the second ends; and only a single pair of attachment members configured to attach the implant to the fractured bone, wherein a first of the pair of attachment members is connected to and extends beyond the first end of the rod in a first direction substantially parallel to the longitudinal axis, and a second of the pair of attachment members is connected to and extends beyond the second end of the rod in a second direction substantially parallel to the longitudinal axis;

wherein a cross section of the first attachment member has a first rotational orientation about the longitudinal axis, and a cross section of the second attachment member has a second rotational orientation, angularly offset from the first rotational orientation, about the longitudinal axis.

15. An implant for setting a fractured bone, comprising:
a substantially rigid rod having a first end and a second end, opposed to the first end, and having a longitudinal axis extending between the first and the second ends; and only a single pair of attachment members configured to attach the implant to the fractured bone, wherein a first of the pair of attachment members is connected to and extends beyond the first end of the rod in a first direction substantially parallel to the longitudinal axis, and a second of the pair of attachment members is connected to and extends beyond the second end of the rod in a second direction substantially parallel to the longitudinal axis;

wherein the rod includes a first rod portion having the longitudinal axis in a plane, the first attachment member has a first longitudinal axis, which is parallel to the longitudinal axis of the first rod portion and distanced from the plane, and the second attachment member has a second longitudinal axis, which is parallel to the longitudinal axis of the first rod portion and distanced from the plane.

16. The implant according to claim 15, wherein:
the pair of attachment members are separated by the rod so as to be attachable to only distal opposed ends of the fractured bone.

* * * * *